US008557829B2

(12) United States Patent
Rodemer

(10) Patent No.: US 8,557,829 B2
(45) Date of Patent: Oct. 15, 2013

(54) USE OF ALLOPURINOL FOR THE TREATMENT OF PALMAR PLANTAR ERYTHRODYSESTHESIA

(75) Inventor: Yolanda Rodemer, Wilhemshaven Rustersiel (DE)

(73) Assignee: Nobera Pharma, S.L., Madrid (ES)

( * ) Notice: Subject to any disclaimer, the term of this patent is extended or adjusted under 35 U.S.C. 154(b) by 0 days.

(21) Appl. No.: 13/114,768

(22) Filed: May 24, 2011

(65) Prior Publication Data

US 2011/0224237 A1 Sep. 15, 2011

Related U.S. Application Data

(62) Division of application No. 12/227,807, filed as application No. PCT/EP2007/055367 on May 31, 2007, now Pat. No. 7,973,046.

(30) Foreign Application Priority Data

Jun. 1, 2006 (EP) .................................... 06011432
May 8, 2007 (EP) .................................... 07107744

(51) Int. Cl.
*A61K 31/519* (2006.01)
(52) U.S. Cl.
USPC ..................................................... 514/262.1
(58) Field of Classification Search
USPC ..................................................... 514/262.1
See application file for complete search history.

(56) References Cited

U.S. PATENT DOCUMENTS

| 4,943,575 | A | 7/1990 | Cremer |
| 6,060,083 | A | 5/2000 | Dorr et al. |
| 6,419,913 | B1* | 7/2002 | Niemiec et al. ............ 424/78.07 |
| 6,685,917 | B2 | 2/2004 | Rosenthal et al. |
| 6,979,688 | B2 | 12/2005 | Ford |
| 2002/0119104 | A1 | 8/2002 | Rosenthal et al. |
| 2003/0060486 | A1 | 3/2003 | Jacob et al. |
| 2003/0113280 | A1 | 6/2003 | Kleen et al. |
| 2003/0157191 | A1 | 8/2003 | Kil et al. |
| 2004/0214215 | A1 | 10/2004 | Yu et al. |
| 2005/0142093 | A1 | 6/2005 | Skover et al. |
| 2006/0177374 | A1 | 8/2006 | Curd et al. |
| 2006/0178351 | A1 | 8/2006 | Curd et al. |

FOREIGN PATENT DOCUMENTS

| JP | 3106817 | 5/1991 |
| JP | 0606700 | 2/2006 |
| WO | 9405291 | 3/1994 |
| WO | 9405293 | 3/1994 |
| WO | 2004110380 | 12/2004 |

OTHER PUBLICATIONS

Kamau et al. (BMC Pharmacology (2001).*
International Search Report issued by the International Searching Authority (ISA/O.E.P.M.) on Aug. 10, 2007, 2007 in connection with International Application No. PCT/ES2007/070097.
DE 102 00 578 A1 (Roehm GMBH [DE]) Jul. 10, 2003.
WO 03/018102 A2 (Vectura Ltd [GB]; Tobyn Michael John [GB]; Staniforth John Wicolas [GB]) Mar. 6, 2003.
WO 2006/030439 A (Biomas Ltd [IL]; Albeck Michael [IL]; Sredni Benjamin [IL]) Mar. 23, 2006.
El-on J. et al., "Development of Topical Treatment for Cutaneous Leishmaniasis Caused by Leishmania-Major in Experimental Animals" Antimicrobial Agents and Chemotherapy, vol. 26, No. 5, 1984, pp. 745-751, XP009075856 ISSN:0066-4804.
Dagher G. et al., "Allopurinol Mouthwash and Vaginal Cream for 5-Fu-Induced Mucositis" Canadian Journal of Hospital Pharmacy, vol. 40, No. 5, 1987, p. 189, XP009075859 ISSN:0008-4123.
Gilbar P., "Palmar-plantar erythrodysesthesia" Journal of Oncology Pharmacy Practice 2003 United States, vol. 9, No. 4, 2003, pp. 137-150, XP002410373 ISSN:1078-1552.
Tsavaris N. et al., "Concomitant Administration of 4 Hydroxypyrazolopyrimidine Allopurinol and High-Dose Continuous Infusion 5 Flurouracil" Oncology (Basel), vol. 47, No. 1, 1990, pp. 70-74, XP009075852 ISSN:0030-2414.
Chin, S.F., "Use of "Bag Balm" as Topical Treatment of Palmar-Planrtar Erythrodysesthesia Syndrome (PPES) in Patients Receiving Selected Chemotherapeeutic Agents", Proc Am Soc Clin Oncol., (2001); 20: Abstract 1623.
Hanawa, T., "Development of patient-friendly preparations: preparation of a new allopurinol mouthwash containing polyethylene(oxide) and carrageenan", Drug Dev Ind Pharm., (2004); 30(2):151-61, Abstract.
Lauman MK et al., "Effect of Pyridoxine on the Incidence of Palmar Plantar Erythroderma (PPE) in Patients Receiving Capecitabine", Proc Am Soc Clin Oncol. (2001); 20: Abstract.
Nagore, E. et al., "Antineoplastic Therapy-Induced Palmar Plantar Erythrodysesthesia ('Hand-Foot') Syndrome", Am J. Clin Dermatol. (2000);1(4):225-34.
Porta, C., M.D., "Allopurinol Mouthwashes in the Treatment of 5-Fluorouracil-Induced Stomatitis", Am J. Clin Oncol. (1994) 17(3):246-7.
Webster-Gandy, J.D., "Palmar-plantar erythrodysesthesia (PPE): A literature review with commentary on experience in a cancer centre", European Journal of Oncology Nursing (2007); 11(3); 238-46.
Wilkes, G.M., "Palmar-Plantar Erythrodysesthesia", Clinical J. Oncol. Nursing (2005); 9(1):103-106.
Woolley, P.V., "A controlled trial of the effect of 4-hydroxypyrazolopyrimidine (allopurinol) on the toxicity of a single bolus dose of 5-fluorouracil", J. Clin Oncol. (1985) 3(1):103-9.
European Search Report issued by the International Searching Authority (ISA/O.E.P.M.) on Dec. 18, 2006 in connection with International Application No. PCT/EP2006/011432.

(Continued)

*Primary Examiner* — Shirley V Gembeh
(74) *Attorney, Agent, or Firm* — Gary J. Gershik; Cooper & Dunham LLP

(57) ABSTRACT

Use of allopurinol or a pharmaceutically acceptable salt thereof for the treatment or prevention of palmar plantar erythrodysesthesia induced by chemotherapy. The allopurinol or its salt is administered topically to the affected areas, palms and soles, preferably in the form of a cream.

22 Claims, No Drawings

(56) References Cited

OTHER PUBLICATIONS

WO 03/045334 A2 (Sound Pharmaceuticals Incorporated), published Jun. 5, 2003.
EP 0 757 910 A1 (Hisamitsu Pharmaceutical Co. Inc., published Feb. 12, 1997.
Hanawa, T., "Development of patient-friendly preparations and Characterization of Allopurinol Gelatin Ge. Containing Polyethylene(oxide)", J. Pharm Sci. Technol., Jps., (2000); vol. 60 No. 3, pp. 175-182.

El-Habet, A.E., "Biochemical Studies on Bilharzial and Nonbiharzial Hyperoxaluria: Effect of Pyridoxine and Allopurinol Treatement", Biochemical Medicine and Metabolic Biology, (1987); vol. 38, pp. 1-8.
Tsavaris, N., "Decreased Oral Toxicity with the Local Use of Allopurinol in Patients W ho Received High Dose 5-Fluorouracil", Selective Cancer Therapeutics, 1991, vol. 7, No. 3, pp. 113-117.

* cited by examiner

USE OF ALLOPURINOL FOR THE TREATMENT OF PALMAR PLANTAR ERYTHRODYSESTHESIA

This application is a divisional of U.S. Ser. No. 12/227,807, filed Jun. 22, 2009, now U.S. Pat. No. 7,973,046 a §371 national stage of PCT International Application No. PCT/EP2007/055367, filed May 31, 2007, which claims priority of European Patent Application Nos. EP07107744.0, filed May 8, 2007 and EP06011432.9, filed Jun. 1, 2006, the contents of all of which are hereby incorporated by reference into this application.

FIELD OF THE INVENTION

The present invention relates to the field of therapy, especially in oncology. It relates to the use of allopurinol or its pharmaceutically acceptable salts for the treatment or prevention of chemotherapy-induced palmar plantar erythrodysesthesia (PPE). It also relates to pharmaceutical compositions comprising allopurinol and to methods for the treatment of PPE.

BACKGROUND OF THE INVENTION

Cancer is a group of diseases in which abnormal cells divide without control. Cancer cells can invade nearby tissues and can spread through the bloodstream and lymphatic system to other parts of the body. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system.

Several treatments are available for cancer, including surgery and radiation for localised disease, and drugs that destroy cancer cells (chemotherapy). Chemotherapy plays a significant part in cancer treatment, as it is required for the treatment of advanced cancers with distant metastasis and often helpful for tumor reduction before surgery (neoadjuvant therapy). It is also used following surgery or radiation (adjuvant therapy) to destroy any remaining cancer cells or prevent recurrence of the cancer.

Many anti-cancer drugs have been developed based on various modes of action: alkylating agents that act directly on the DNA (such as cisplatin, carboplatin, oxaliplatin, busulfan, chlorambucil, cyclophosphamide, ifosfamide, dacarbazine); antimetabolites that interfere with DNA and RNA synthesis (such as 5-fluorouracil, capecitabine, 6-mercaptopurine, methotrexate, gemcitabine, cytarabine (ara-C), fludarabine); anthracyclines that interfere with enzymes involved in DNA replication (such as daunorubicin, doxorubicin, epirubicin, idarubicin, mitoxantrone); microtubule disrupters (taxanes such as paclitaxel and docetaxel or Vinca alkaloids such as vinblastine, vincristine, and vinorelbine); topoisomerase inhibitors (such as etoposide, doxorubicin, topotecan and irinotecan); hormone therapy (such as tamoxifen, flutamide) and recently introduced targeted therapy (such as the inhibitors of EGFR cetuximab, gefitinib or the protein tyrosine kinase inhibitor imatinib) are the most frequently used.

Cancer chemotherapy may consist of a single drug or combinations of drugs that are delivered in cycles. A cycle consists of treatment with one or more drugs followed by a period of rest.

The development of chemotherapy in the last decades has significantly improved the treatment of cancer, resulting in effective treatments in some types of cancers, and improved survival or time to progression in others. Currently, most chemotherapy is administered intravenously; however, oral chemotherapy drugs are gaining wider use.

Unfortunately, most chemotherapy drugs cannot difference between a cancer cell and a healthy cell. Therefore, chemotherapy often affects the body's normal tissues and organs which results in complication of treatments, or side effects. In addition to the problems they cause, side effects can prevent doctors from delivering the prescribed dose of chemotherapy, reducing the probability of a correct treatment of cancer. Most frequent side effects of chemotherapy are anemia, neutropenia, thrombocytopenia, fatigue, alopecia, nausea and vomiting, mucositis and pain.

Palmar plantar Erythrodysesthesia (PPE) was first described by Zuehlke in 1974 as a erythematous eruption of the palms and soles associated with mitotane therapy (Zuehlke, R. K. *Dermatologica*, 1974, 148(2), 90-92). PPE is a distinctive and relatively frequent toxic reaction related to some chemotherapeutic agents. It is a painful swelling and erythematous rash, located in the palms and soles, often preceded by dysesthesia, usually in the form of a tingling sensation, and often associated with edema. The rash may become bollous and then desquamate without scarring, and pain gradually increases. Erythema may also occur in periungal areas. Generally it is confined to the hands and feet, the hands are usually more severely affected than the feet.

Histologically PPE shows mild spongiosis, scattered necrotic and dyskeratotic keratynocites and vacuolar degeneration of the basal layer. Dermal changes in most cases include dilated blood vessels, papillary edema, and a sparse superficial perivascular limphohistiocytic infiltrate that can be found in varying degrees in the epidermis.

PPE is clearly distinct from other adverse skin reactions and is reviewed in Nagore E. et al, *Am J Clin Dermatol*. 2000, 1(4), 225-234 which is incorporated herein by reference in its entirety.

The severity of PPE can be classified according to the following WHO grades:
1. Dysesthesia/paresthesia, tingling in the hands and feet.
2. Discomfort in holding objects and upon walking, painless swelling or erythema.
3. painful erythema and swelling of palms and soles, periungual erythema and swelling.
4. Desquamation, ulceration, blistering, severe pain.

Another grading is based on the US National Cancer Institute criteria:
1. Skin changes or dermatitis without pain (E.g erythema, peeling)
2. Skin changes with pain, not interfering with function
3. Skin changes with pain interfering with function Among the agents that have been reported to cause PPE, Fluorouracil (5-FU), Capecitabine (Xeloda®), pegylated Liposomal doxorubicin (Caelyx®/Doxil®), Cytarabine (Cytosar-U®), Floxuridine (FUDR®), Tegafur and Idarubicin (Idamycin®) are the most frequent inducers.

Fluorouracil is a fluorinated pyrimidine that is metabolized intracellularly to its active form, fluorouridine monophosphate, that inhibits DNA synthesis. It is indicated for several types of cancer, among others as adjuvant or palliative therapy in breast, colorectal, gastric and pancreatic cancer. The benefits of fluorouracil based adjuvant chemotherapy in reducing the risk of relapse and prolonging survival in patients with resected colon cancer are well established, particularly in stage III disease, Survival advantages were demonstrated with bolus intravenous fluorouracil (425 mg/m$^2$) plus leucovorin (a biomodulator) according to the Mayo Clinic regimen (five days, monthly, for six months), or the Roswell par regimen (weekly bolus, six of every eight weeks, for eight months) (Sun W. et al *Curr Oncol Rep.* 2005 May; 7(3):181-5). For metastatic colon cancer a 24 hour continuous infusion of high dose 5-FU (2600 mg/m$^2$) and leucovorin weekly for 6 weeks followed by a 1 or 2 week rest period (AIO protocol) showed improved progression free survival compared with the Mayo protocol (Köhne et al *J Clin Oncol,* 2003, vol 21, no. 20, 3721-3728).

New combinations of fluorouracil are emerging, such as with oxaliplatin (FOLFOX) or irinotecan (FOLFIRI) showing survival benefits in the treatment of colorectal cancer (Goldberg, *Oncologist* 2005; 10 Suppl 3:40-8. Review). Most of these combinations use infusional fluorouracil.

In spite of the obvious benefits of Fluorouracil as a chemotherapy, the incidence of PPE is frequent with the bolus and high dose continuous infusion regimens. This is a reason for dose reduction or interruption of the treatment. In metastatic colon cancer, the prolonged 5-FU$_{24H}$/LV schedule resulted in higher incidence of PPE (34%) compared with the Mayo protocol (13%) (*J Clin Oncol,* 1998, vol 16, 3537-3541). Infusional fluorouracil is also responsible for PPE in the treatment of breast cancer, see for example Smith I E et al. *Ann. Oncol.* 2004, 15(5) 751-758.

Capecitabine (Xeloda®) is a prodrug, an oral fluoropyrimidine carbonate that is activated into fluorouracil in tumor tissue by thymidine phosphorylase. It is used as adjuvant therapy for the treatment of colon cancer, as first line therapy for metastatic colorectal cancer, and for the treatment of advanced or metastatic breast cancer. In a recently reported phase III study, capecitabine was compared with fluorouracil+leucovorin (Mayo protocol) as adjuvant treatment for stage III colon cancer (Twelves C. et al., *N Engl J Med* 2005, 352, 2696-2704). Concerning efficacy, capecitabine was shown to be equivalent to fluorouracil+leucovorin. As first line treatment for metastatic colorectal cancer, capecitabine achieved response rates superior to those achieved with the Mayo Clinic regimen with equivalent progression free survival and overall survival (Van Cutsem E. et al. *Br J Cancer* 2004, 90:1190-1197). Concerning toxicity, in both cases capecitabine showed less incidence of severe grade 3 or 4 stomatitis and neutropenia. However, the incidence of hand-foot syndrome (PPE) was significantly higher with capecitabine than with fluorouracil+leucovorin, being as high as 49-60% for all grades and 17% for severe grades. This resulted in dose reduction, delay or interruption of the treatment. In metastatic breast cancer the same situation arises, capecitabine alone or in combination with docetaxel showed improved efficacy versus docetaxel, but one of the most common dose limiting adverse effects is PPE.

In view of the above, although capecitabine has the important advantage of being an oral drug and more convenient for the patient, in particular in combination treatments, palmar planar erythrodysesthesia remains one of the main causes for concern when using this drug.

Another drug that is frequently associated with PPE is pegylated liposomal doxorubicin, i.e. doxorubicin hydrochloride encapsulated in long-circulating stealth liposomes with surface bound methoxypolyethylene glycol. The pegylation protects the liposomes from detection by the immune system allowing them to reach a tissue or organ characterized by a higher permeability of the endothelium, such as a tumor. Liposomal doxorubicin is used for the treatment of advanced ovarian cancer and of metastatic breast cancer. PPE with this drug is related to the schedule, and the incidence is relatively high: 37.4% for all grades, with 16.4% for severe grades were reported in ovarian cancer. Toxicity can be reduced by a reduction in dose intensity (for example from 50 mg/m$^2$ every 4 weeks to 40 mg/m$^2$, Rose P G, *The Oncologist,* 2005, 10:205-214).

Palmar plantar erythrodysesthesia is thus an important side effect for the mentioned chemotherapeutic agents. However, little is known of its causes and at present there is no therapy or prophylaxis for PPE proved to be effective. Chemotherapy reduction, delay or withdrawal can be effective in reducing or eliminating PPE, but at the cost of seriously compromising the chemotherapeutic treatment of cancer.

Some of the few treatments that have been proposed are: cold compresses or ice packs, especially during chemotherapy; elevating hands or feet; skin hydration; emollient skin creams containing lanolin, lactic acid, petroleum jelly (for example Bag Balm® a petroleum lanolin based ointment with hydroxyquinoline sulfate as antiseptic ingredient, or Aquaphor®), and topical or oral corticosteroids such as dexamethasone.

Pyridoxine (vitamin B6) has been used to decrease the pain from PPE (Fabian et al. *Invest. New Drugs* 1990, 8:57-63; Lauman M K et al. *ASCO Proceedings,* 2001, abstract 1565) and it appears to provide some symptomatic benefit in patients being treated with capecitabine.

Amifostine, a cytoprotective agent, has been used to try to prevent PPE in patients being treated with liposomal doxorubicin (Lyass O. et al, *ASCO Proceedings,* 2001, abstract 2148).

U.S. Pat. No. 6,060,083 discloses the use of topical DMSO for the treatment of PPE, in particular when caused by pegylated liposomal doxorubicin.

U.S. Pat. No. 6,979,688 describes the topical use of uracil ointment for the treatment of PPE induced by fluorouracil or a precursor thereof.

None of the proposed treatments has yet been able to effectively treat or prevent PPE. It is clear that an effective treatment of PPE is still needed, in order to untie the full potential of chemotherapeutic agents such as fluorouracil, capecitabine or pegylated liposomal doxorubicin and the different regimens and combinations in which they are used.

Allopurinol is a structural isomer of hypoxanthine, that inhibits xanthine oxidase, an enzyme that converts oxypurines to uric acid. By blocking the production of uric acid, this agent decreases serum and urine concentrations of uric acid, thereby providing protection against uric acid-mediated end organ damage in conditions associated with excessive production of uric acid. It has been used for many years for the treatment or prevention of gout, hyperuricemia and kidney stones, through oral or parenteral systemic administration.

Allopurinol has also been reported for the treatment of mucositis, a frequent chemotherapy- or radiation-induced damage to the rapidly dividing cells lining the mouth, throat and gastrointestinal (GI) tract. Allupurinol is used in the form of mouthwashes (dispersion in water) (porta C. et al, *Am J clin Oncol.* 1994, Vol 17, no. 3, 246-247). An improved formulation for mouthwashes comprising allopurinol, carboxymethylcellulose and water is described in JP-3106817. Hanawa et al. in *Drug Dev Ind Pharm* 2004, 30(2) 151-161 describe another mouthwash comprising allopurinol, polyethyleneoxide and carrageenan.

Dagher et al., canadian journal of Hospital pharmacy, vol. 40, no. 5 1987, page 189 discloses the use of allopurinol mouthwash and vaginal 0.1% cream for the treatment of 5-FU-Induced mucositis.

Allopurinol has also been administered systemically to modulate the 5-fluorouracil myelosuppresion, in particular granulocytopenia (Woolley at al. *J. of Clinical Oncology*, 1985 vol. 3, no. 1, 103-109). However, preclinical studies showed antagonism between the two drugs.

EP278040 describes the use of pteridines or xanthine oxidase inhibitors, among other allopurinol, for the treatment of genetically caused, degenerative retina diseases such as retinopathia pigmentosa, in the form of topically administrable eye drops or eye creams. There is no specific disclosure in this document of a topical composition containing allopurinol.

WO94/05293 and WO94/05291 describe synergistic compositions comprising methylsuphonylmethane (MSM) and at least one of oxypurinol or allopurinol and their use for the treatment of skin conditions, diseases and injuries such as burns, dermatitis, hyperkeratosis, sun exposure, skin ageing, etc. Oxypurinol or allopurinol are described as enhancing the skin healing or repairing properties of MSM.

None of the cited documents mentions or suggests that allopurinol would be useful for the treatment or prevention of palmar planar erythrodysesthesia.

SUMMARY OF THE INVENTION

The inventor has surprisingly found that allopurinol, when applied topically to the palms and soles of the patient, is very effective in the treatment and prevention of palmar planar erythrodysesthesia induced by fluoropyrimidine chemotherapy. As show in the examples, topical application of allopurinol to cancer patients being treated with chemotherapy completely avoided the appearance of PPE.

In one aspect the invention is directed to use of allopurinol or a pharmaceutically acceptable salt thereof in the manufacture of a medicament for the treatment or prevention of palmar plantar erythrodysesthesia induced by fluoropyrimidine chemotherapy.

In a second aspect, the invention is directed to a pharmaceutical composition for the topical administration to the hands and feet, comprising from 1-10% by weight of allopurinol or a pharmaceutically acceptable salt thereof, with the proviso that it does not comprise methylsulphonylmethane or cetomacrogol.

In a third aspect, the invention is directed to a method for treating or preventing palmar plantar erythrodysesthesia induced by fluoropyrimidine chemotherapy in a patient affected or likely to be affected by this syndrome, comprising topically applying to the hands and feet a therapeutically effective amount of allopurinol or a pharmaceutically acceptable salt thereof.

DETAILED DESCRIPTION OF THE INVENTION

Palmar plantar erythrodysesthesia (PPE) is also known as acral erythema, hand-foot syndrome, palmar planar erythema, Burgorf's syndrome, and toxic erythema of the palms and soles. In the context of the present invention, the term palmar plantar erythrodysesthesia include all these synonyms when they describe conditions related to chemotherapy as described above.

In the context of the present invention the term allopurinol refers also to the different tautomers of the compound, since it is a tautomeric mixture of 1H-pyrazolo[3,4-d]pyrimidin-4-ol and 1,5-dihydro-4H-pyrazolo[3,4-d]pyrimidin-4-one:

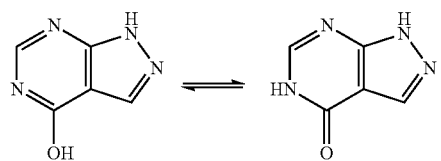 [SMILES: Oc1ncnc2[nH]ncc12 ; O=c1[nH]cnc2[nH]ncc12]

As mentioned above, the topical application of allopurinol or one of its pharmaceutically acceptable salt has surprisingly been found to be useful for the treatment and prevention of PPE.

Thus, in one aspect the invention is directed to use of allopurinol or a pharmaceutically acceptable salt thereof in the manufacture of a medicament for the treatment or prevention of palmar plantar erythrodysesthesia induced by fluoropyrimidine chemotherapy.

In one embodiment the medicament is in the form of a cream. Preferably the cream is an hydrophylic cream.

In another embodiment the medicament is for the treatment of PPE induced by fluorouracil, capecitabine, either alone or in combination with other agents.

The medicament is thus useful for the treatment of patients suffering from cancer, preferably from colorectal cancer, ovarian cancer, breast cancer, gastric and pancreatic cancer and receiving chemotherapy, either as adjuvant, neoadjuvant or palliative. Example of patients and chemotherapies inducing PPE have been discussed in the section background of the invention and is incorporated herein. The medicament for the treatment of PPE is particularly useful in patients receiving or about to receive infusional 5-FU, capecitabine, either alone or in combination with other agents.

In another embodiment, the medicament for the treatment of PPE induced by pegylated doxorubicin, particularly in patients receiving or about to receive pegylated doxorubicin.

Without willing to be bound by theory, it is believed that when applied topically to the palms and soles, allopurinol acts locally at the level of the epidermis, inhibiting the metabolism of the cytotoxic drugs.

The toxicity to the palms and soles, characteristic of PPE, may be due to a specific local enzymatic activity of this skin area, the enzymes being probably involved in the metabolism of the cytotoxic drugs. Keratinocytes made up 90% of epidermal cells. It is important to note that the keratinocytes of the palms and soles have a specific phenotype, such as production of keratin 9, hypopigmentation and thick suprabasal layers that diferenciates them from the keratinocytes of other parts of the skin.

Schwartz et al, in *Biochem Pharmacol*, 1988, 37, 353-355 have shown that human keratinocytes have a higher Thymidine Phosphorylase (TP) activity, that is not present in other animals. This activity is responsible of the salvage of thymidine for DNA synthesis. Other studies show a strong expression of TP in the basal layer of the epidermis.

Thymidine phosphorylase is an enzyme involved in the activation of 5'DFUR (a metabolite of capecitabine) into 5-FU. It can also be involved in the activation of 5-FU. Thymidine phosphorylase (TP) is markedly upregulated in many solid tumors such as colorectal, breast and kidney cancers, locally activating prodrugs of fluoropyrimidines that "target" the tumors. This enzyme is also known as the angiogenic platelet-derived endothelial cell growth factor (PD-ECGF), that stimulates endothelial cell migration in vitro and angiogenesis in vivo and plays an important role in tumour progression and metastasis.

Fischel et al. *Anti Cancer Drugs* 2004, 15 969-974 propose that capecitabine toxicity in the palms and soles may be due to the elevated TP activity in the skin, in particular in these areas where it is known that epidermal renewal is particularly active. According to this hypothesis high levels of cell proliferation and TP activity can be present in this cutaneous area, inducing angiogenesis and drug metabolism. Thus, if the tissue of the palms and soles shows similarities with tumor tissue, it is plausible that the chemotherapeutic agents have increased specific toxic activity against the keratinocytes of the palms and soles in the same way as they target proliferating tumor tissue.

Our hypothesis is that when administered topically allopurinol acts directly or indirectly inhibiting the enzyme thymidine phosphorylase. Interestingly, Allopurinol has been described in Gallo et al. *J Biological Chemistry* 1968, vol. 243, 4943-4951, to be a selective inhibitor of deoxythymidine phosphorylase, another name for the enzyme thymidine phosphorylase. It inhibits TP but not uridine phosphorylase.

Allopurinol could be acting by a reduction of the local production of active toxic metabolites that can be responsible for the symptoms of PPE. Local application allows an effective targeting of the affected areas, and avoids the toxicities and complications that systemic allopurinol can provoke in cancer patients, in particular it avoids interfering with the chemotherapy.

In one embodiment the treatment is for reducing or preventing PPE in patients being treated systemically with chemotherapy comprising an agent selected from Fluorouracil (5-FU) or Capecitabine (Xeloda®).

In another embodiment the treatment is for reducing or preventing PPE in patients being treated systemically with chemotherapy comprising Liposomal pegylated doxorubicin (Doxil®, Caelyx®).

The invention further relates to a topical pharmaceutical composition for the treatment of the hands and feet, comprising from 1%-10% by weight of allopurinol or a pharmaceutically acceptable salt thereof, together with at least one topically acceptable carrier material, with the proviso that it does not comprise methylsulphonylmethane or cetomacrogol.

Allopurinol is a compound very slightly soluble in water and alcohol; practically insoluble in chloroform and in ether; it dissolves in dilute solutions of alkali hydroxides. It can be used as such, or, to improve the solubility in water, a salt such as the sodium salt can be used instead of the base.

In the topical compositions of the invention, allopurinol or its salt is typically present in an amount of from about 1 up to 10%, in particular form 1-8%, more particularly from 1-6%, especially from 1 up to 5%. Below 1% the concentration of allopurinol is not sufficient to treat or prevent effectively PPE. In concentrations above 10% the allopurinol can have undesired side effects for the skin of the patient.

A preferred range is from 2 up to 5%, more preferably from 2-4% of the total composition on a weight basis. An amount of about 3% has given good results and is especially preferred. All percentages given are weight-% (w/w), if not indicated otherwise.

Pharmaceutical compositions of the invention, suitable for topical administration to the hands and feet, preferably to the palms and soles, are for example creams, lotions, ointments, microemulsions, fatty ointments, gels, emulsion-gels, pastes, foams, tinctures, solutions, patches, bandages and transdermal therapeutic systems. Most preferred are creams or emulsion-gels.

Creams or lotions are oil-in-water emulsions. Oily bases that can be used are fatty alcohols, especially those containing from 12 to 18 carbon atoms, for example lauryl, cetyl or stearyl alcohol, fatty acids, especially those containing from 10 to 18 carbon atoms, for example palmitic or stearic acid, fatty acid esters, e.g. glyceryl tricaprilocaprate (neutral oil) or cetyl palmitate, liquid to solid waxes, for example isopropyl myristate, wool wax or beeswax, and/or hydrocarbons, especially liquid, semi-solid or solid substances or mixtures thereof, for example petroleum jelly (petrolatum, Vaseline) or paraffin oil. Suitable emulsifiers are surface-active substances having predominantly hydrophilic properties, such as corresponding non-ionic emulsifiers, for example fatty acid esters of polyalcohols and/or ethylene oxide adducts thereof, especially corresponding fatty acid esters with (poly)ethylene glycol, (poly)propylene glycol or sorbitol, the fatty acid moiety containing especially from 10 to 18 carbon atoms, especially partial glycerol fatty acid esters or partial fatty acid esters of polyhydroxyethylene sorbitan, such as polyglycerol fatty acid esters or polyoxyethylene sorbitan fatty acid esters (Tweens), and also polyoxyethylene fatty alcohol ethers or fatty acid esters, the fatty alcohol moiety containing especially from 12 to 18 carbon atoms and the fatty acid moiety especially from 10 to 18 carbon atoms, such as polyhydroxyethyleneglycol fatty acid ester (for example Tagat S), or corresponding ionic emulsifiers, such as alkali metal salts of fatty alcohol sulfates, especially having from 12 to 18 carbon atoms in the fatty alcohol moiety, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia agents that prevent the creams from drying out, for example humectants, such as polyalcohols, such as glycerol, sorbitol, propylene glycol and/or polyethylene glycols, and also preservatives, perfumes, gelling agents, etc.

Ointments are water-in-oil emulsions that contain up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax or beeswax. Emulsifiers are corresponding lipophilic substances, for example of the type indicated above, such as sorbitan fatty acid esters (Spans), for example sorbitan oleate and/or sorbitan isostearate. Additives to the aqueous phase are, inter alia humectants, such as polyalcohols, for example glycerol, propylene glycol sorbitol and/or polyethylene glycol, and also preservatives, perfumes, etc.

Microemulsions are isotropic systems based on the following four components: water, a surfactant, for example a tensioactive, a lipid, such as a non-polar or polar oil, for example paraffin oil, natural oils such as olive or maize oil, and an alcohol or polyalcohol containing lipophilic groups, for example 2-octyldodecanol or ethoxalated glycerol or polyglycerol esters. If desired, other additives may be added to the microemulsions. Microemulsion have micelles or particles with sizes below 200 nm and are transparent or translucid systems, the form spontaneously and are stable.

Fatty ointments are water-free and contain as base especially hydrocarbons, for example paraffin, petroleum jelly and/or liquid paraffins, also natural or partially synthetic fat, such as fatty acid esters of glycerol, for example coconut fatty acid triglyceride, or preferably hardened oils, for example hydrogenated groundnut oil, castor oil or waxes, also fatty acid partial esters of glycerol, for example glycerol mono- and di-stearate, and also, for example, the fatty alcohols increasing the water-absorption capacity, emulsifiers and/or additives mentioned in connection with the ointments.

With gels, a distinction is made between aqueous gels, water-free gels and gels having a low water content, which gels consist of swellable, gel-forming materials. There are used especially transparent hydrogels based on inorganic or organic macromolecules. High molecular weight inorganic components having gel-forming properties are predominantly water-containing silicates, such as aluminium silicates, for example bentonite, magnesium aluminium silicates, for example Veegum, or colloidal silicic acid, for example Aerosil. As high molecular weight organic substances there are used, for example, natural, semisynthetic or synthetic macromolecules. Natural and semi-synthetic polymers are derived, for example, from polysaccharides containing a great variety of carbohydrate components, such as celluloses, starches, tragacanth, gum arabic and agar-agar, and gelatin, alginic acid and salts thereof, for example sodium alginate, and derivatives thereof, such as lower alkylcelluloses, for example methyl- or ethyl-cellulose, carboxy- or hydroxy-lower alkylcelluloses, for example carboxymethyl- or hydroxyethyl-cellulose. The components of synthetic gel-forming macromolecules are, for example, suitably substituted unsaturated aliphatic compounds such as vinyl alcohol, vinylpyrrolidine, acrylic or methacrylic acid.

Emulsion-gels—also called "emulgels"—represent topical compositions which combine the properties of a gel with those of an oil-in-water emulsion. In contrast to gels, they contain a lipid phase which due to its fat-restoring properties enables the formulation to be massaged in whilst, at the same time, the direct absorption into the skin is experienced as a pleasant property. Furthermore, one can observe an increased solubility for lipophilic active ingredients. One advantage of emulsion-gels over oil-in-water emulsions resides in the enhanced cooling effect which is brought about by the coldness due to evaporation of the additional alcohol component, if present.

Foams are administered, for example, from pressurised containers and are liquid oil-in water emulsions in aerosol form; unsubstituted hydrocarbons, such as alkanes, for example propane and/or butane, are used as propellant. As oil phase there are used, inter alia hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters (Tweens), and emulsifiers having predominantly lipophilic properties, such as sorbitan fatty acid esters (Spans). The customary additives, such as preservatives, etc., are also added.

Tinctures and solutions generally have an ethanolic base, to which water may be added and to which there are added, inter alia, polyalcohols, for example glycerol, glycols and/or polyethylene glycol, as humectants for reducing evaporation, and fat-restoring substances, such as fatty acid esters with low molecular weight polyethylene glycols, propylene glycol or glycerol, that is to say lipophilic substances that are soluble in the aqueous mixture, as a replacement for the fatty substances removed from the skin by the ethanol, and, if necessary, other adjuncts and additives. Suitable tinctures or solutions may also be applied in spray form by means of suitable devices. In this case, due to the solubility problems of allopurinol, a salt is more appropriate for tinctures or solutions.

Transdermal therapeutic systems with—in particular—local delivery of allopurinol contain an effective amount allopurinol optionally together with a carrier. Useful carriers comprise absorbable pharmacological suitable solvents to assist passage of the active ingredient through the skin, Transdermal delivery systems are, for example, in the form of a patch comprising (a) a substrate (=backing layer or film), (b) a matrix containing the active ingredient, optionally carriers and optionally (but preferably) a special adhesive for attaching the system to the skin, and normally (c) a protection foil (=release liner). The matrix (b) is normally present as a mixture of all components or may consist of separate layers.

All these systems are well known to the person skilled in the art. The manufacture of the topically administrable pharmaceutical preparations is effected in a manner known per se, for example by dissolving or suspending allopurinol in the base or, if necessary, in a portion thereof.

The compositions according to the invention may also comprise conventional additives and adjuvants for dermatological applications, such as preservatives, especially paraben esters like methylparaben, ethylparaben, propylparaben, butylparaben, or quaternary ammonium compounds like benzalkonium chloride, or formaldehyde donors like imidazonidinyl urea, or alcohols like benzyl alcohol, phenoxyethanol or acids like benzoic acid, sorbic acid; acids or bases used as pH buffer excipients; antioxidants, especially phenolic antioxidants like hydroquinone, tocopherol and derivatives thereof, as well as flavonoids, or miscellaneous antioxidants like ascorbic acid, ascorbyl palmitat; perfumes; fillers such as kaolin or starch; pigments or colorants; UV-screening agents; moisturizers, especially glycerin, butylen glycol, hexylen glycol, urea, hyaluronic acid or derivatives thereof; anti-free radical agents such as vitamin E or derivatives thereof; penetration enhancers especially propylene glycol; ethanol; isopropanol; dimethylsulfoxide; N-methyl-2-pyrrolidone; fatty acids/alcohols such as oleic acid, oleyl alcohol; terpenes such as limonen, menthol, 1-8 cineole; alkyl esters such as ethyl acetate, butyl acetate; ion pairing agents such as salicylic acid.

Further details concerning suitable topical formulations may be obtained by reference to standard textbooks such as Banker and Rhodes (Ed) *Modern Pharmaceutics* $4^{th}$ ed. (2002) published by Marcel Dekker Inc.; *Harry's Cosmeticology* (2000), 8th Edition, Chemical Publishing Co.; *Remington's Pharmaceutical Sciences* $20^{th}$ ed Mack Publishing Co. (2000).

In a preferred embodiment allopurinol is formulated as a cream, preferably in an emollient base provided the emollient base is suitable for topical application on the skin, is substantially non-toxic and provides a suitable carrier for allopurinol or its pharmaceutically acceptable salts. A properly chosen emollient base may also provide a certain amount of relief in itself. In a particular case, a moisturizing cream is preferred as a base.

Emollients may be e.g. fatty alcohols, hydrocarbons, triglycerides, waxes, esters, silicone oils and lanolin containing products. Fatty alcohols are e.g. cetyl alcohol, octyldodecanol, stearyl alcohol and oleyl alcohol. Hydrocarbons include mineral oil, petrolatum, paraffin, squalene, polybutene, polyisobuten, hydrogenated polyisobutene, cerisin and polyethylene. Triglycerides are e.g. castor oil, caprylic/capric triglyceride, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadamia nut oil, olive oil, apricot kernel oil, hazelnut oil and borage oil. Waxes include e.g. carnauba wax, beeswax, cadelilla wax paraffin, Japan wax, microcrystalline wax, jojoba oil, cetyl esters wax, and synthetic jojoba oil. Esters include e.g. isopropyl myristate, isopropyl palmitate, octyl palmitate, isopropyl linoleate, 12-15 alcohol benzoates, cetyl palmitate, myristyl myristate, myristyl lactate, cetyl acetate, propylene glycoldicaprylate/caprate, decyl oleate, stearyl heptanoate, diisostearyl malate, octylhydroxystearate and isopropyl isostearate. Silicone oils are e.g. dimethicone (dimethyl polysiloxane) and cyclomethicone, Lanolin containing products are e.g. lanolin, lanolin oil, isopropyl lanolate, acetylated lanolin alcohol, acetylated lanolin, hydroxylated lanolin, hydrogenated lanolin and lanolin wax.

In a preferred embodiment allopurinol is prepared by mixing it with a commercial basic cream such as Bag Balm or Basiscreme DAC (Deutsches Arzneimittel codex).

The daily dosage of the topical formulation comprising allopurinol or its pharmaceutically acceptable salts may depend on various factors, such as sex, age, weight and individual condition of the patient, as well as the chemotherapy he is being or will be given.

The topical pharmaceutical compositions, e.g. in the form of creams, emulsion-gels or gels may be applied once, twice or three times daily, but also more frequent daily applications such as 5 to 10 times a day are possible provided that the symptoms of PPE are avoided. The dosage may be variable, in function of the severity of the PPE symptoms, or the cycles or dosages of the chemotherapeutic treatment.

The pharmaceutical composition of the invention is administered to patients already suffering from PPE in its different grades, or as a preventive treatment to patients susceptible to develop PPE as a consequence of a chemotherapeutic treatment that is administered or about to be administered.

The administration can be intensified shortly before, during and after chemotherapeutic treatment, when the risks of developing PPE are higher, and can be reduced during periods of rest between cycles.

The invention will be further illustrated by means of examples, they should no be taken as limiting the scope of the invention as defined by the claims.

EXAMPLES

Example 1

Preparation of a Topical Formulation Comprising Allopurinol

A formulation was prepared by suspending allopurinol base (3% by weight of total formulation) in 5% water and then adding Basiscreme DAC (92%) and mixing.

The composition of the Basic cream DAC is as follows:
Glycerolmonostearate: 4.0
Cetylalcohol 6.0
Medium chain triglyceride 7.5
White Vaseline 25.5
Polyoxyethylenglycerol monostearate 7.0
Propylenglycol 10.0
Water 40.0

The resulting cream is distributed in suitable containers and stored. The cream is easily applicable by the patients.

Example 2

Treatment of Palmar Planar Erythrodysesthesia

Patients with colorectal carcinoma were administered chemotherapy (adjuvant or palliative) following the usual protocols. As soon as the first symptoms of palmar planar erythrodysesthesia appeared after starting chemotherapy, the patients were administered the cream prepared in example 1.

The characteristics of the patients treated with the cream and the chemotherapeutic regimen that they were administered were as follow:
Patients with advanced or metastatic colorectal cancer: 8
Patients with resected stage III colon cancer: 2
Chemotherapy:
   5FU+LV bolus (Mayo protocol): 1 patient
   5FU+LV infusional (AIO protocol): 7 patients
   Capecitabine monotherapy: 2 patients The cream was applied 5 times per day, to the palms and soles, as long as the chemotherapy was applied. The frequency was reduced in between cycles and increased shortly before and during chemotherapy administration.

Results: following the topical treatment with allopurinol, the symptoms of PPE disappeared and the chemotherapy could be completed without any dose reduction or delay in the treatment due to PPE. This is most remarkable in the case of patients being treated with high dose infusional $5FU_{24H}$+leucovorin, were the incidence of PPE has been reported to be as high as 34%.

Example 3

Treatment of Palmar Planar Erythrodysesthesia

Patients suffering from colon cancer or breast cancer were treated from January 2005 up to March 2007 with the following standard chemotherapy:
   AIO protocol: high dose infusion $5FU_{24H}$+leucovorin
   FOLFOX 4 protocol: day 1: oxaliplatin, 85 mg/m2, and leucovorin, 200 mg/m2, concurrently i.v., then 5-FU, 400 mg/m2 i.v. bolus followed by 600 mg/m2 continuous i.v.; day 2: leucovorin, 200 mg/m2 i.v., then 5-FU, 400 mg/m2 i.v. bolus, followed by 600 mg/m2 continuous i.v.; repeated every 2 weeks.
Oral capecitabine.

The patient characteristics are summarized in table 1.

TABLE 1

| Patients characteristics | |
|---|---|
| | n |
| Patients | 35 |
| Age | |
| Median | 67 |
| range | (42-83) |
| ECOG performance | |
| 0 | 21 |
| 1 | 14 |
| 2 | 0 |
| Sex | |
| Male | 11 |
| female | 24 |
| Tumor type | |
| Breast Cancer | 8 |
| Colon Cancer | 27 |
| Prior Chemotherapy | |
| Yes | 10 |
| No | 25 |
| Regimes Therapie | |
| 5-FU: AIO | 16 |
| FOLFOX 4 | 7 |
| Capecitabine | 12 |

Palmar plantar erythrodysesthesia (PPE) appeared in 30% of the patients treated with 5-FU and in 66% of those treated with capecitabine. The time of appearance and the severity of the symptoms was variable, it is summarized in table 2.

TABLE 2

Palmar plantar erythrodysesthesia

|  | n | % |
|---|---|---|
| Patients |  |  |
| Total | 35 |  |
| PPE symptoms | 15(35) | 42% |
| AIO | 5(16) | 31% |
| FOLFOX 4 | 2(7) | 28% |
| Capecitabine | 8(12) | 66% |
| PPE Toricity grade (NCI) |  |  |
| 1 | 1 | 6.6% |
| 2 | 5 | 33% |
| 3 | 9 | 60% |
| Cumulative Dosis 5-FU regimen until appearance of PPE AIO |  |  |
| Median | 42.000 mg |  |
| Range | (23.000 mg-64.800 mg) |  |
| FOLFOX 4 |  |  |
| Median | 40.000 mg |  |
| Range | (38.000 mg-42.000 mg) |  |
| Cumulative dosis with capecitabine until apprearauce of PPE |  |  |
| Median | 81.000 mg |  |
| Range | (35.000 mg-180.000 mg) |  |

These data correlate well with the reported incidence of PPE.

The cream comprising allopurinol as prepared in example 1 was topically applied by the patients 4-5 times a day to the hands and feet. In case of no response to this treatment and persistence of PPE symptoms, the dosage of chemotherapy was reduced and some cases interrupted. The response is summarized in table 3.

TABLE 3

Response to allopiirinol treatment

|  | n | % |
|---|---|---|
| PPEPatients | 15 |  |
| (TR) | 13 | 86.6% |
| (CR) | 10 | 66.6% |
| (PR) | 3 | 20.0% |
| (NR) | 2 | 13.3% |
| AIO | 5 |  |
| (TR) | 5 | 100% |
| (CR) | 4 | 80% |
| (PR) | 1 | 20% |
| (NR) | 0 | 0% |
| FOLFOX-4 | 2 |  |
| (TR) | 1 | 50% |
| (CR) | 0 |  |
| (PR) | 1 | 50% |
| (NR) | 1 | 50% |
| Capecitabine | 8 |  |
| (TR) | 7 | 87% |
| (CR) | 5 | 62.5% |
| (PR) | 2 | 25% |
| (NR) | 1 | 12.5 |

TR: total response CR: complete remission PR: Partial remission NR: no response

In 86% of the patients there was a response to the treatment, with a reduction of the symptoms in 20% and complete disappearance in 66%.

No toxics effects associated to the topical allopurinol treatment were observed, and the compliance of the patients and improvements of the PPE symptoms were surprising. As a result quality of life significantly improved.

In 86% of the patients that had developed PPE, the treatment with allopurinol allowed the completion of chemotherapy as planned.

The invention claimed is:

1. A pharmaceutical composition for topical administration to the skin of a subject to treat chemotherapy-induced palmar plantar erythrodysesthesia (PPE) (hand and foot syndrome), comprising 1-10% by weight of the pharmaceutical composition of allopurinol or a pharmaceutically acceptable salt thereof, wherein the pharmaceutical composition is formulated for topical administration to the skin of a subject, and is free of methylsulfonylmethane or cetomacrogol.

2. The pharmaceutical composition of claim 1, comprising about 1-8% by weight of the composition of allopurinol or a pharmaceutically acceptable salt thereof.

3. The pharmaceutical composition of claim 2, comprising about 1-5% by weight of the composition of allopurinol or a pharmaceutically acceptable salt thereof.

4. The pharmaceutical composition of claim 3, comprising about 2-4% by weight of the composition of allopurinol or a pharmaceutically acceptable salt thereof.

5. The pharmaceutical composition of claim 1, further comprising pyridoxine.

6. The pharmaceutical composition of claim 1, in the form of a hydrophylic cream.

7. The pharmaceutical composition of claim 1, in the form of a cream.

8. A pharmaceutical composition for topical administration to the skin of a subject to treat chemotherapy-induced palmar plantar erythrodysesthesia (PPE) (hand and foot syndrome), comprising 1-10% by weight of the pharmaceutical composition of allopurinol or a pharmaceutically acceptable salt thereof, wherein the pharmaceutical composition is formulated for topical administration to the skin of a subject, and is free of methylsulfonylmethane and cetomacrogol.

9. The pharmaceutical composition according to claim 8, additionally comprising pyridoxine.

10. The pharmaceutical composition according to claim 8, in the form of a cream.

11. The pharmaceutical composition according to claim 8, in the form of a hydrophilic cream.

12. The pharmaceutical composition according to claim 8, comprising from about 1-8% by weight of the composition of allopurinol or a pharmaceutically acceptable salt thereof.

13. The pharmaceutical composition according to claim 12, comprising from about 1-5% by weight of the composition of allopurinol or a pharmaceutically acceptable salt thereof.

14. The pharmaceutical composition according to claim 13, comprising from about 2-4% by weight of the composition of allopurinol or a pharmaceutically acceptable salt thereof.

15. The pharmaceutical composition according to claim 8, comprising about 3% by weight of the composition of allopurinol or a pharmaceutically acceptable salt thereof.

16. The pharmaceutical composition according to claim 15, additionally comprising pyridoxine.

17. The pharmaceutical composition according to claim 15, in the form of a cream.

18. The pharmaceutical composition according to claim 15, in the form of a hydrophilic cream.

19. The pharmaceutical composition according to claim 8, comprising about 8% by weight of the pharmaceutical composition of allopurinol or a pharmaceutically acceptable salt thereof.

20. A pharmaceutical composition according to claim 19, additionally comprising pyridoxine.

21. A pharmaceutical composition according to claim 19, in the form of a cream.

22. A pharmaceutical composition according to claim 19, in the form of a hydrophilic cream.

\* \* \* \* \*